United States Patent [19]
Rammler

[11] Patent Number: 5,472,427
[45] Date of Patent: Dec. 5, 1995

[54] TROCAR DEVICE

[76] Inventor: David H. Rammler, 30 Oak Hill Dr., Woodside, Calif. 94062

[21] Appl. No.: 142,192

[22] Filed: Oct. 22, 1993

[51] Int. Cl.[6] .............................. A61M 5/170; A61M 5/00
[52] U.S. Cl. ........................... 604/164; 604/264; 606/182
[58] Field of Search ................................ 604/164, 264, 604/157; 606/182

[56] References Cited

U.S. PATENT DOCUMENTS

| | | | |
|---|---|---|---|
| 2,699,784 | 1/1955 | Krayl | 606/182 |
| 4,411,653 | 10/1983 | Razi | 604/157 |
| 4,931,042 | 6/1990 | Holmes et al. | 604/164 |
| 5,030,206 | 7/1991 | Lander | 604/164 |
| 5,066,288 | 11/1991 | Deniega et al. | 604/274 |
| 5,112,321 | 5/1992 | Hiltebrandt | 604/264 |
| 5,114,407 | 5/1992 | Burbank | 604/164 |
| 5,141,496 | 8/1992 | Dalto et al. | 604/157 |
| 5,203,773 | 4/1993 | Green | 604/104 |
| 5,209,736 | 5/1993 | Stephens et al. | 604/164 |
| 5,215,526 | 6/1993 | Deniega et al. | 604/164 |
| 5,217,441 | 6/1993 | Shichman | 604/283 |
| 5,242,427 | 9/1993 | Bilweis | 604/264 |
| 5,312,354 | 5/1994 | Allen et al. | 604/157 |

*Primary Examiner*—John G. Weiss
*Attorney, Agent, or Firm*—Flehr, Hohbach, Test, Albritton & Herbert

[57] ABSTRACT

A trocar device is disclosed which is adapted for insertion into a body cavity, such as the abdominal cavity, without the need for cavity insufflation. The trocar device comprises applicator and trocar components. The trocar components comprises a cylindrical trocar tube and detachable obdurator. The applicator comprises a housing into which the trocar and obdurator are loaded prior to insertion, and means for applying a force, such as a spring or electric motor, to drive the obdurator and trocar through the body wall into the cavity. Various electrical and mechanical means are provided for limiting the penetration depth of the obdurator. In one embodiment, sonic transducer means are provided for detecting a phase change in reflected sonic waves at the internal body wall boundary to stop trocar penetration. Several alternative embodiments of the apparatus and method of use are disclosed.

11 Claims, 10 Drawing Sheets

FIG. —1

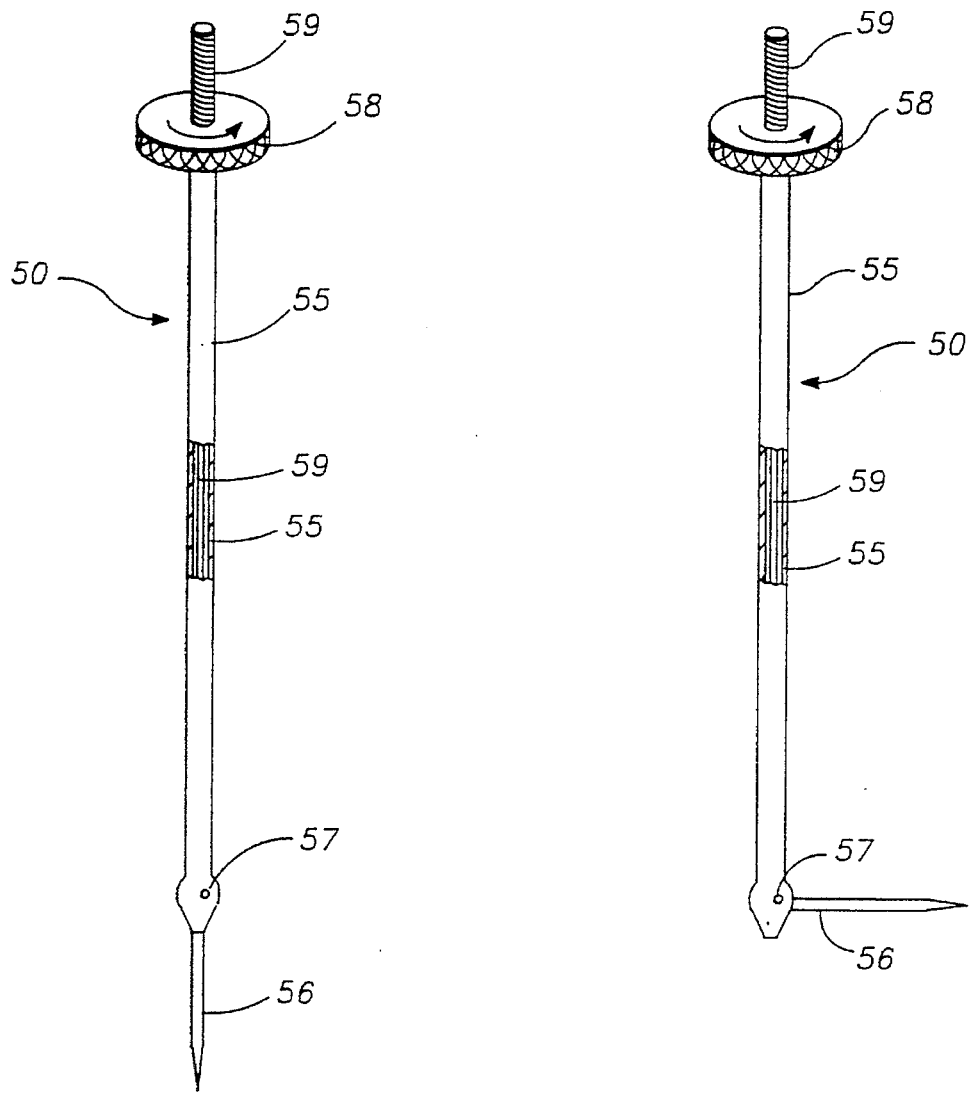
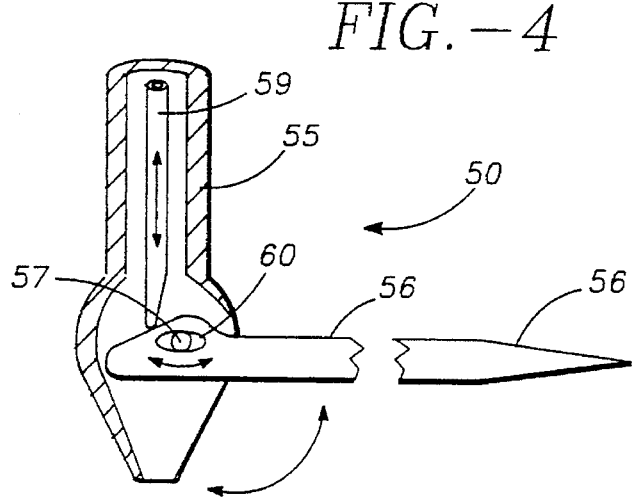
FIG.-3  FIG.-4
FIG.-5

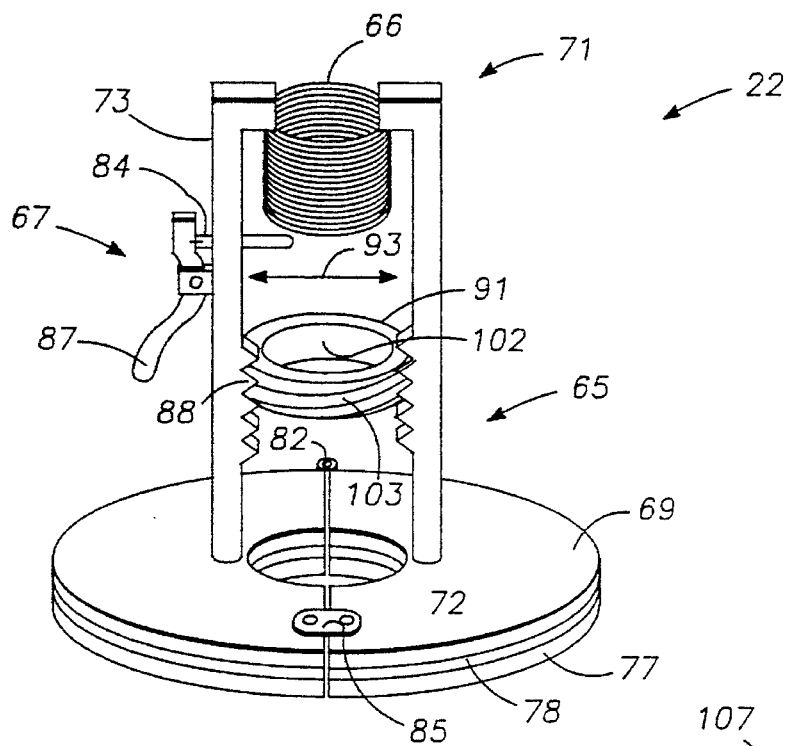
FIG.-8
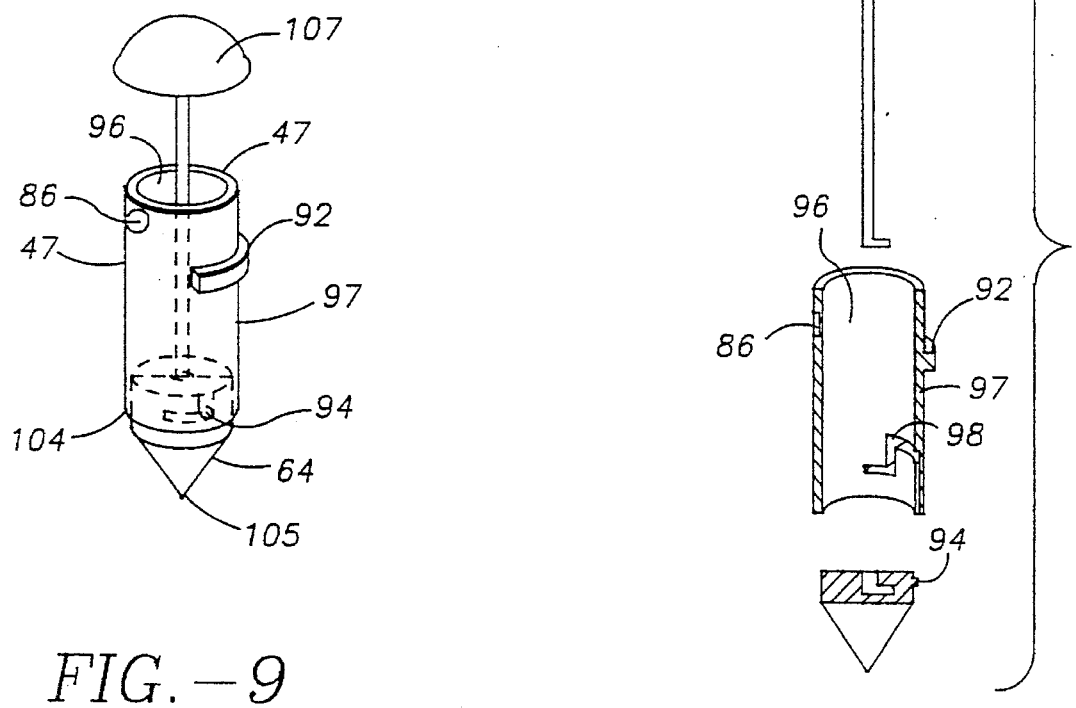
FIG.-9
FIG.-10

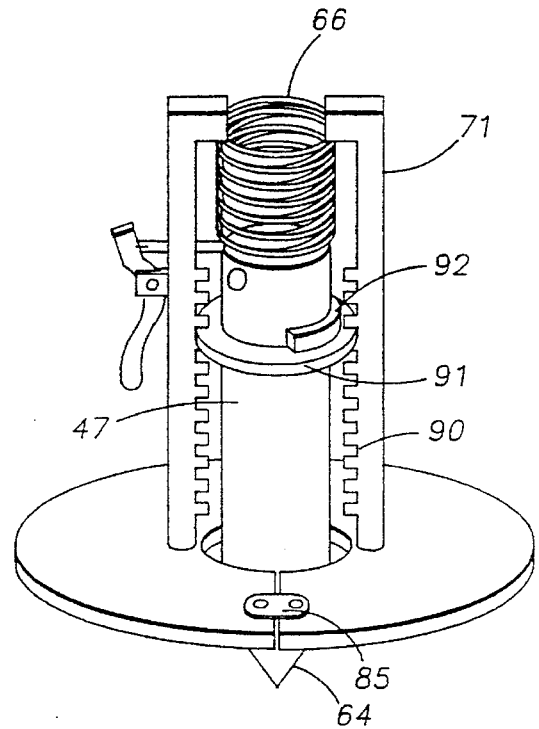
FIG.—12
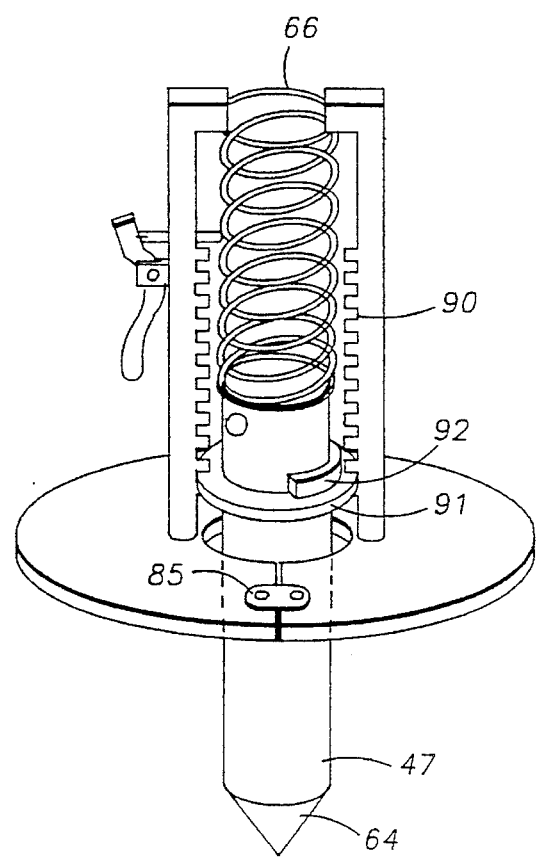
FIG.—13

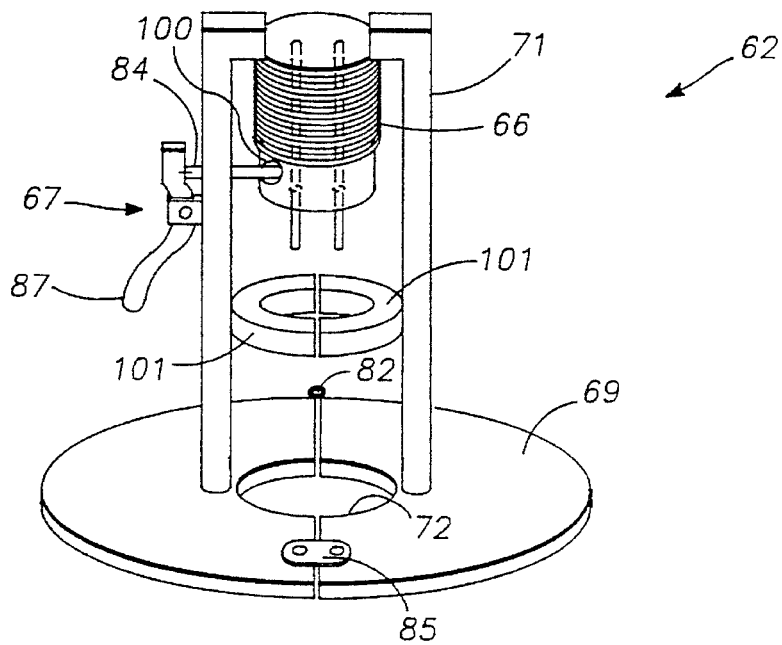
FIG.—14
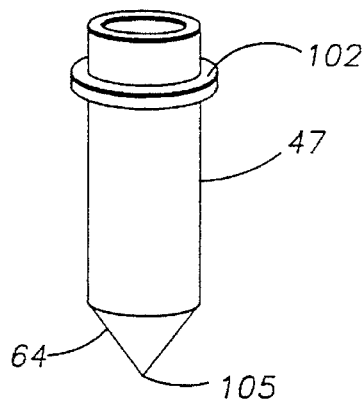
FIG.—15
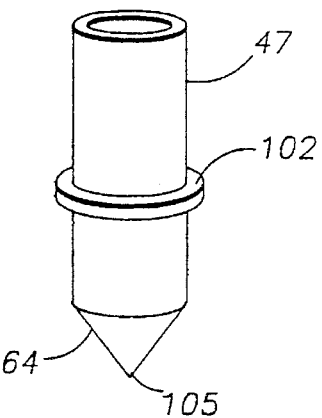
FIG.—16
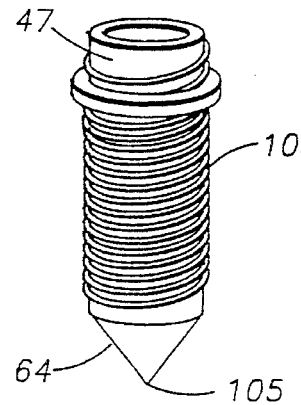
FIG.—17

TROCAR DEVICE

INTRODUCTION

1. Technical Field

The field of this invention is surgical instrumentation for maintaining the abdominal wall away from the abdominal viscera.

2. Background

Trocars are sharp instruments used to puncture and maintain an opening into a body cavity. For example, the opening may be needed for draining fluids, or to provide access for surgical instruments during endoscopic procedures. Conventional gas-type trocars are used in conjunction with a procedure involving insufflation of the body cavity wherein a cannula is inserted into the body cavity through a small incision and the cavity inflated with gas passed through the cannula. The cannula is removed, and an obdurator housed within the bore of a trocar tube is thrust into the inflated cavity. The obdurator is then removed and an instrument is inserted into the abdominal cavity through the trocar tube. A trocar of this conventional type has a valve to maintain the inflated condition of the cavity. This need for a valve is problematic because the trocar valve is an expensive component of the conventional trocar. The need for a valve may also restrict the types of surgical instruments that can be inserted through the trocar. It is of interest to provide improved apparatus and methods for carrying out the insufflation process and trocar manipulation.

SUMMARY OF THE INVENTION

The present invention provides a trocar system, including a simple gas-valve-free trocar device, and a surgical rack system and methods for using them.

Accordingly, one aspect of the invention is a trocar device comprising a trocar applicator, and a trocar tube and obdurator assembly. The obdurator is removably joined to the tube and has a piercing tip which extends from the front end of the elongate tube. The tube and obdurator assembly is enclosed by the applicator and is triggered to move between a normally retracted position in which the obdurator tip is protected and an extended position in which the obdurator tip is exposed. Force means in the applicator is coupled to the trocar so that the tube and associated obdurator are driven into the body cavity when the force means is triggered. Adjustable penetration depth limiting means is provided to limit the penetration depth of the obdurator.

In another aspect, a rack system is provided for opening a void space within the cavity without conventional gas insufflation so that a gas-valve-free trocar may be driven into the cavity while controlling the trocar movement to avoid cutting internal organs. This capability is provided by cross-beams extending over the skin which overlays the cavity, and which are adjustably attached to a horizontal rack. Attaching means for attaching to the skin are provided and are mounted to the cross-beams. An adherent tape is interposed between the attaching means and the skin to adhere them to each other. Lifting hooks may optionally be used to engage internal surfaces of the abdominal cavity to aid in opening the void space.

The horizontal rack is coupled to a vertical supporting means which provides movement relative to a platform which supports the patient. Moving the cross beams in synchronous movement up from the abdomen raises the abdominal wall away from the viscera so that when the trocar pierces the abdominal wall, it does not cut the viscera. Means are provided for one or more trocars to be securely attached to the cross-beams; the abdominal wall tissue and trocars are held in alignment by the cross beams.

DESCRIPTION OF THE DRAWINGS

FIG. 3 shows an L-shaped lifting rod in its linear pre-insertion configuration.

FIG. 4 shows the L-shaped lifting rod in FIG. 4 in its non-linear post-insertion configuration.

FIG. 5 shows an exemplary mechanical mechanism, somewhat schematic, for transforming between the linear and non-linear lifting rod configurations shown in FIG. 3 and FIG. 4.

FIG. 8 shows the trocar applicator alone of the trocar device shown in FIG. 6.

FIG. 9 shows the trocar tube and obdurator alone of the trocar device shown in FIG. 6.

FIG. 10 shows a sectional view of the trocar tube and obdurator of the trocar device shown in FIG. 6.

FIG. 12 shows an embodiment of a trocar device with the slip-ring depth penetration limiting means adjusted for slight penetration into the abdominal wall.

FIG. 13 shows the embodiment of a trocar device in FIG. 12 with the slip-ring depth penetration limiting means adjusted for maximum penetration into the abdominal wall.

FIG. 14 shows an alternative embodiment of a trocar applicator.

FIG. 15 shows an alternative embodiment of a trocar tube and obdurator having a fixed penetration depth for use with the trocar applicator shown in FIG. 14.

FIG. 16 shows an alternative embodiment of a trocar tube and obdurator having a fixed penetration depth less than that of the trocar shown in FIG. 15.

FIG. 17 shows an alternative embodiment of a trocar tube and obdurator having an adjustable penetration depth for use with the trocar applicator shown in FIG. 14.

DESCRIPTION OF THE SPECIFIC EMBODIMENTS

The drawings illustrate a trocar system 21 comprising two primary components: a gas-valve-free trocar apparatus 22 and trocar rack apparatus 23 for using the valve-free trocar in surgical procedures. Rack apparatus 23 is used cooperatively with trocar apparatus 22 to facilitate safe insertion of trocar 22 without insufflation of the body cavity.

Figure 1:
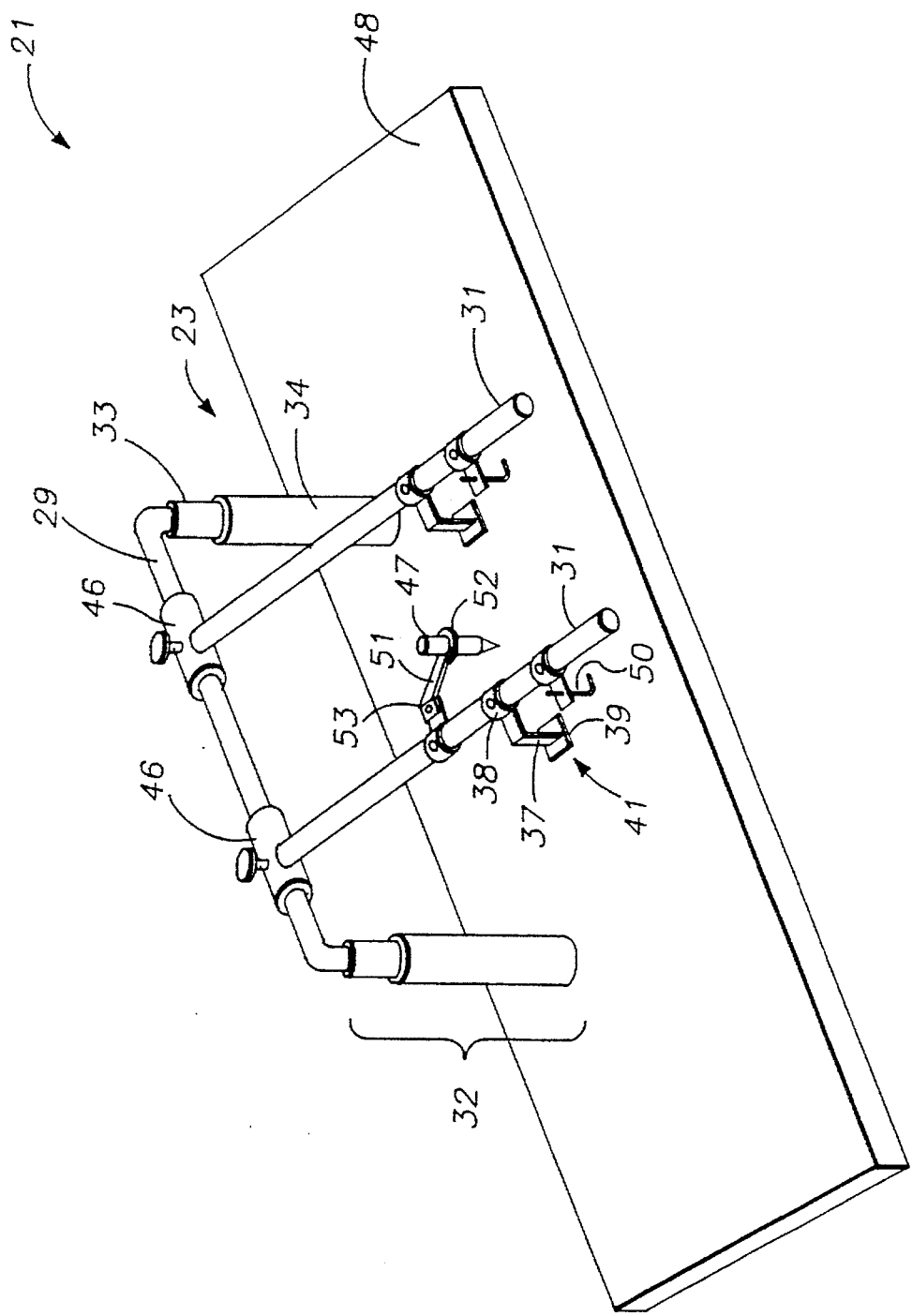
FIG. 1 shows an embodiment of a trocar device and trocar rack apparatus.
Figure 2:
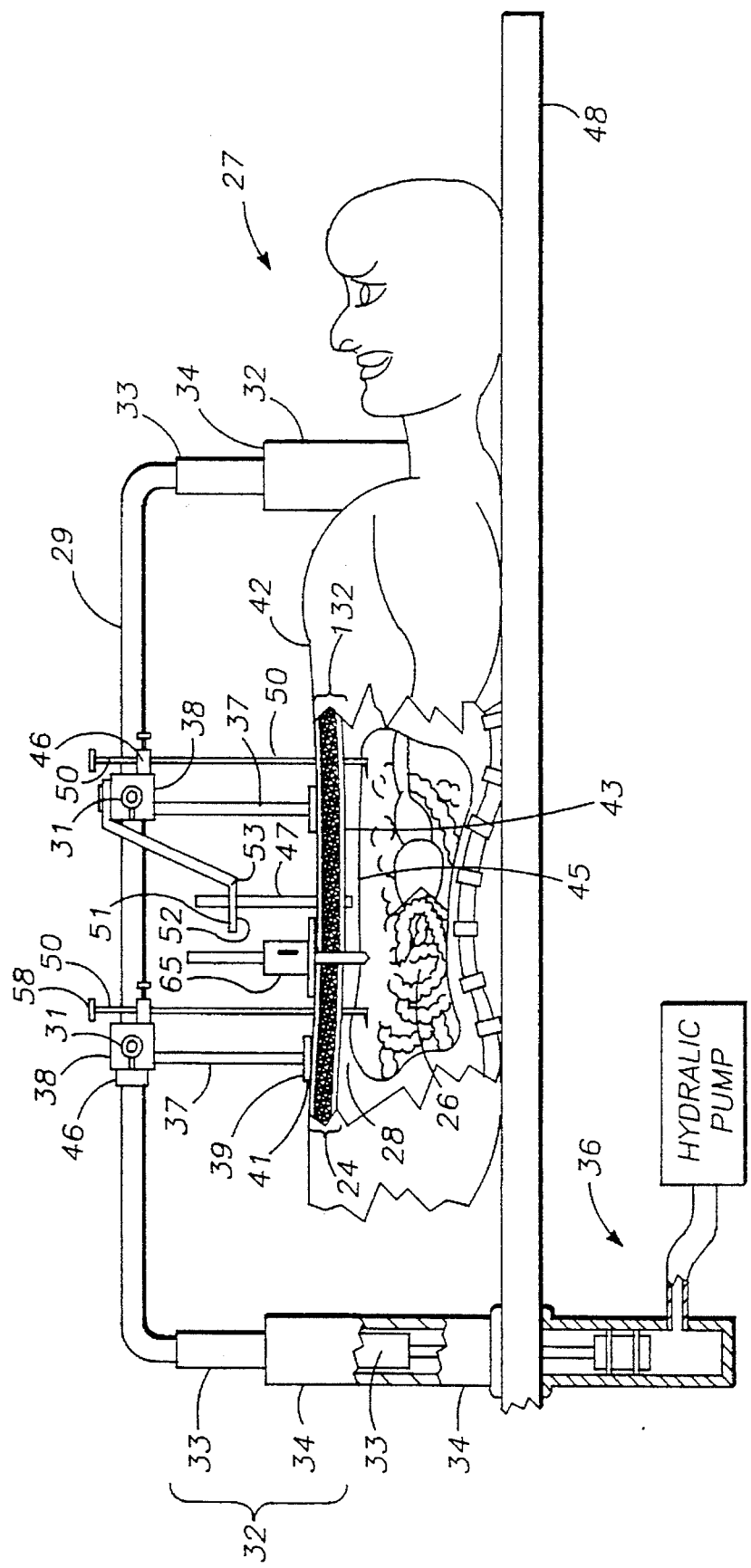
FIG. 2 shows additional detail of portions of the embodiment in FIG. 1 and the relationship of the components to a patient undergoing a surgical procedure.

FIGS. 1–2 are illustrations of an embodiment of trocar mounting rack apparatus 23 for lifting abdominal wall 24 away from abdominal viscera 26 of a patient 27 during surgery without using gas insufflation of the abdominal cavity 28. It will be understood that the devices and methods are not limited to abdominal cavity 28 but may be applied in surgical procedures involving other body cavities and other internal body structures or internal organs. Selected elements shown in FIG. 1 are illustrated with greater detail in FIG. 2.

Trocar rack apparatus 23 comprises a horizontal rack 29, spaced apart horizontal cross-beams 31 supported by rack 29, and vertical supporting means for raising and lowering rack 29 with synchronous movement of cross-beams 31, and attaching means for attaching abdominal wall 24 to cross-beams 31.

Vertical supporting means is provided by two vertical cylindrical beam assemblies 32 in the illustrated embodiment, which are attached to horizontal rack 29 proximal to the upper end of vertical beam assemblies 32. Vertical beam assemblies 32 each comprise nesting inner 33 and outer 34 cylindrical sections adapted to slide with respect to one another. Vertical motive force means, such as one or more electric motors coupled to a threaded post for elevation upon turning, or alternately a rack and pinion type linear motion system, or a suitably connected hydraulic system 36 may be used to synchronously raise or lower inner section 33 connected to horizontal rack 29. Manual means, such as a crank, may also be used. Alternatively, means for raising and lowering cross beams 31 relative to rack 29, may be provided. It will be understood that various structures as are known in the mechanical arts may be used to implement rack 29, vertical supporting means, and cross beams 31, and that the invention is not limited to the particular structures shown.

Attaching means is provided for attaching cross beams 31 to patient 27. For example, an attaching arm 37 is adapted at one end 38 to mount to cross-beam 31 and extends to a second end 39 having a surface adapted to adhere to tape surface 41 adhered to skin 42 of patient 27. An attaching clamp 35 to grasp skin 42 may alternatively be used. The type and number of attaching arms 37 may depend on the surgical procedure and the characteristics of the patient, particularly the size of the abdominal region 44 (e.g. child or adult) and the weight of the abdominal wall 21 to be lifted, including the amount of fat present.

Raising cross-beams 31 causes attaching arm 37 and therefore skin 42, abdominal wall 24 including the parietal peritoneum 43 which lines the abdominal wall, and the visceral peritoneum 45 which lines the abdominal viscera, to raise away from internal abdominal viscera 26. Cross beams 31 may be fixed on rack 29 or may be adjustably mounted.

In the illustrated embodiment, horizontal rack 29 comprises cylindrical members; however, members having other geometrical forms may be used. Similarly, cross-beams 31 are shown as cylindrical beams which are attached via clamps 46 to rack 29 and which extend over the abdominal region 44 where the trocar is inserted, but beams having other geometrical forms, e.g. square, may be used. Preferably at least two cross-beams 31 are used, however more beams or even a single beam may be used; the number depending on the nature of the surgical procedure. A single cross beam 31 may be used if attaching arm 37 mounted to cross beam 31 comprises an elongated structure adapted to extend from cross beam 31 to separated regions of the abdomen 44, or alternatively if cross beam 31 in aligned longitudinally with patient 27.

Trocar rack apparatus 23 may further include one or more trocar mounting means attached to cross-beam 31 for mounting trocar tube 47 in a stable upright position, with or without a surgical instrument (not shown) inserted. Various trocar mounting means are suitable including clamps, ties, clips, collars, and the like. For example, trocar mounting means may comprise an adjustable trocar mounting arm or clamp 51 adapted at one end for mounting to cross beam 31 and having a cylindrical collar 52 at the other end, that can be tightened around a cylindrical trocar tube 47. A pivot 53 may be provided between the two ends of clamp 51 to permit precise positioning of clamp 51 to trocar 47 when inserted into abdominal cavity 28. Trocar tube 47 may be provided with structure on its external surface to couple to clamp 51. For example, a depression or notch 54 on the external cylindrical surface of trocar tube 47 may be provided that engages a spring loaded plunger (not shown) within the internal cylindrical collar 52 of clamp 51 to positively lock trocar tube 47 to clamp 51. Trocar tube 47 may optionally have a greater length than a conventional trocar to facilitate attachment to cross-beam 31.

Trocar rack apparatus 23 may also optionally include supporting platform 48. In the embodiment illustrated in FIGS. 1–2, vertical cylindrical beam assemblies 32 are connected to supporting platform 48. Supporting platform 48 may be a platform as shown, or other type of structure such as a floor surface, or an operating table or portion thereof.

Lifting hooks, such as L-shaped rods 50 may optionally be used to engage internal surfaces of the abdominal cavity, such as the abdominal wall 24, to lift and/or support the abdominal wall and thereby assist in opening and/or maintaining the void space in the abdominal cavity as shown in FIG. 2. The optional use of lifting hooks is of benefit when there is an expectation that the viscera will adhere to the abdominal wall structure or where the weight of the abdominal wall suggests that support in addition to that provided by the tape surface 41 or attaching clamp 35 is of benefit.

The structure of an exemplary L-shaped rod having alternate straight (linear) and L-shaped (non-linear) conformations is illustrated in FIGS. 3 and 4. FIG. 3 illustrates L-shaped rod 50 in its linear configuration (e.g. non-"L-shaped") as it would appear during insertion into a patient, and after removal from the patient. FIG. 4 illustrates the L-shaped rod in non-linear (e.g. L-shaped") configuration as it would appear after insertion while supporting the abdominal wall of a patient. The structure of the rod permits it to be easily inserted into a patient, and to transform between the straight and L-shaped configurations as described hereinafter.

L-shaped rod 50 comprises hollow outer shaft 55, extension 56, pivot dowel 57 which rotatably couples outer shaft 55 to extension 56, adjustment knob 58, and partially threaded internal pin 59. Each element of rod 50 is preferably made of a noncorrosable and sterilizable material, such as stainless steel, or the like. Extension 56 is pivotally coupled to one end of shaft 55 via pivot dowel 57 at a pivot point 60. The pivot point is located between between the two ends of extension 56 to provide the desired fulcrum and mechanical leverage, and to preserve a small cross-sectional area in the region of the pivot so that rod 50 is more easily inserted. Knob 58 is rotatably attached to the other end of shaft 55, and has a threaded hole 61 through its center that engages threads on internal pin 59. Rotation of knob 58 causes pin 59 to move longitudinally within the hollow bore of shaft 55. The length of pin 59 and the location of the pivot point on extension 56 are selected so that as knob 58 is rotated, pin 59 moves along shaft 55 to engage one side of extension 56. Extension 56 undergoes an angular rotation relative to shaft 55 as pin 59 is translated due to the levering action of the pivot as shown in FIG. 5.

The overall length of extension 56 and the position of the pivot point relative to its two ends allows the desired 90 degree rotation of the extension to be accomplished with only a short linear translation of pin 59. The long side of extension 56 is pointed or tapered, such as in the form of a blade or a lance to facilitate insertion through the skin and abdominal wall. While one mechanism for affecting an L-shape to the initially linear rod has been described, other mechanical mechanisms or means for providing the L-shape after insertion may be used with comparable effectiveness, including other means for coupling and adjusting the angle between the shaft and the extension, and shapes other than the "L-shape". For example, a lifting hook having multiple L-shaped extensions may be used, such as a T-shape, a fan shape, and the like.

During surgery, the L-shaped rods are adjustably mounted on cross-beams 31 and extend vertically downward from cross-beams 31 toward patient 27. The L-shaped rods are inserted through surgical incisions into abdominal cavity 28 and provide greater lifting and/or holding ability than attaching arm 37 may provide alone. Each L-shaped rod may be used in conjunction with a sterile adhesive tape 40 to provide a sterile surface region on the skin surrounding the rod insertion site. The tape surfaces 40 may be covered with a pealable layer, such as a sterile polymeric or foil type layer, to preserve sterility. When an L-shaped rod is used with attaching arm 37, adhesive tape 40 may be integral with tape surface 41 interposed between second end 39 of attaching arm 37 and the skin. After insertion of the L-shaped rods and attachment of the attaching arms 37 to the skin, cross-beams 31 are raised, causing L-shaped rods, which extend under parietal peritoneum 43 and optionally under visceral peritoneum 45, to lift and separate the abdominal wall from viscera 26. Alternately, the L-shaped rods may be used alone with a separate adhesive tape surface to effect and maintain separation before and during surgery.

Figure 6:
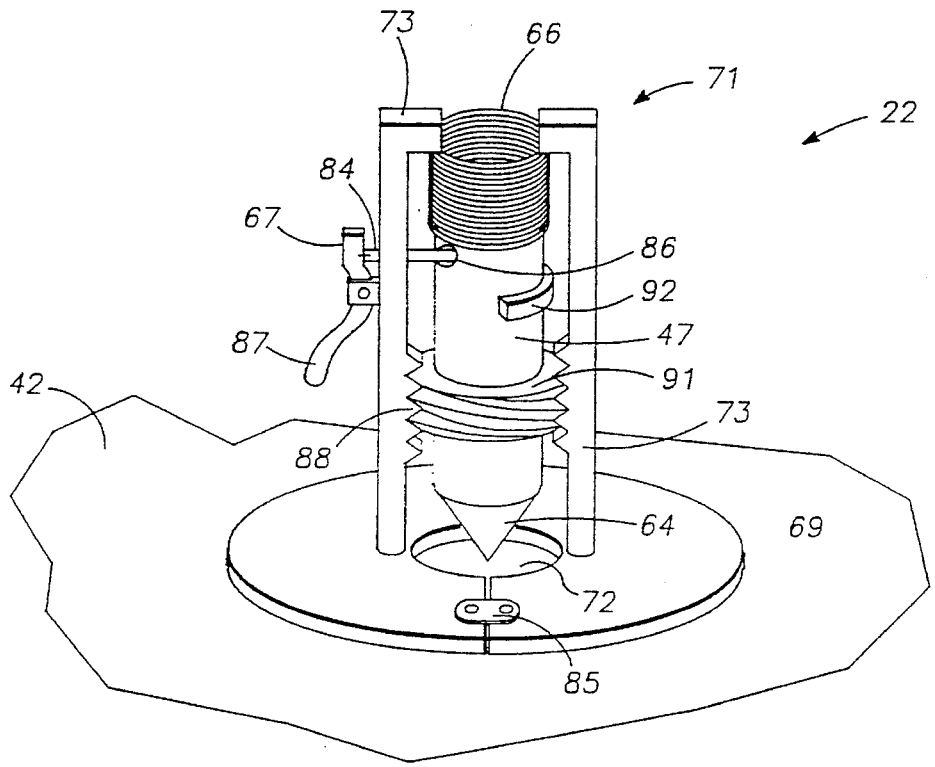
FIG. 6 shows a simple embodiment of a trocar device with the obdurator in its normally retracted position.
Figure 7:
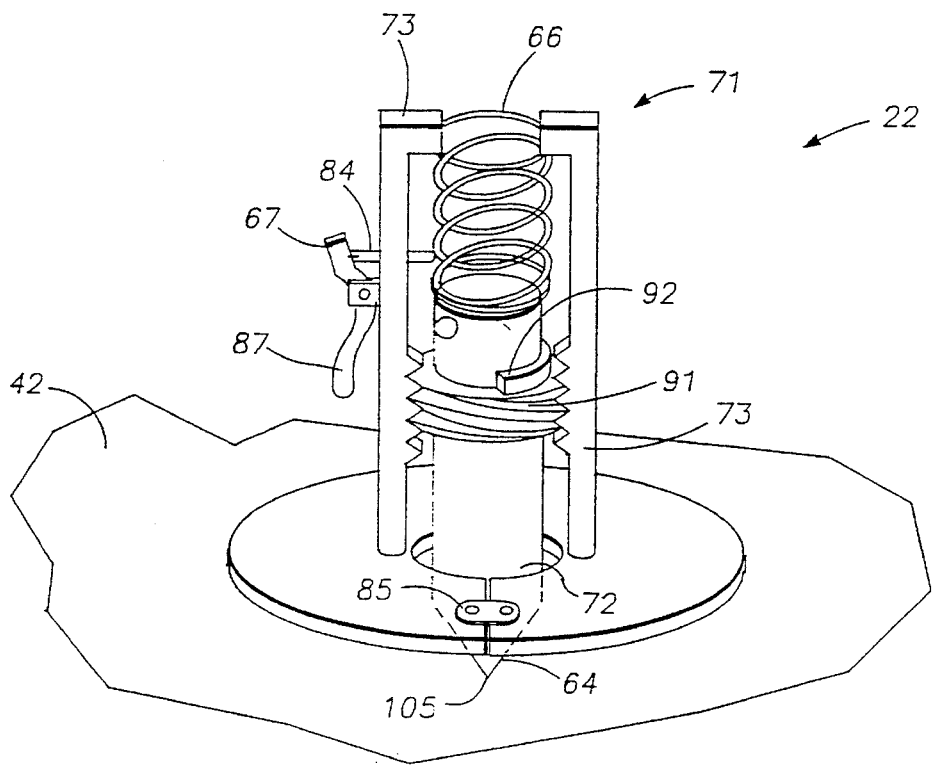
FIG. 7 shows the embodiment in FIG. 6 with the obdurator in its extended position.

FIGS. 6–7 are illustrations of an embodiment of a gas-valve-free trocar device 22 in accordance with one aspect of the invention. Trocar device 22 comprises separable trocar applicator 62 and trocar assembly 63. Trocar assembly 63 comprises trocar tube 47 and obdurator 64. FIG. 6 shows trocar 22 with obdurator 64 in its normally retracted position. FIG. 7 shows trocar 22 with obdurator 64 extended.

FIG. 8 shows applicator 62 without trocar/obdurator assembly 63 installed. Applicator 62 is used for inserting trocar tube 47 and obdurator 64 into abdominal cavity 28 and comprises housing 65, force means such as spring 66, trigger means such as trigger 67, and trocar penetration limiting means 70.

Figure 11:
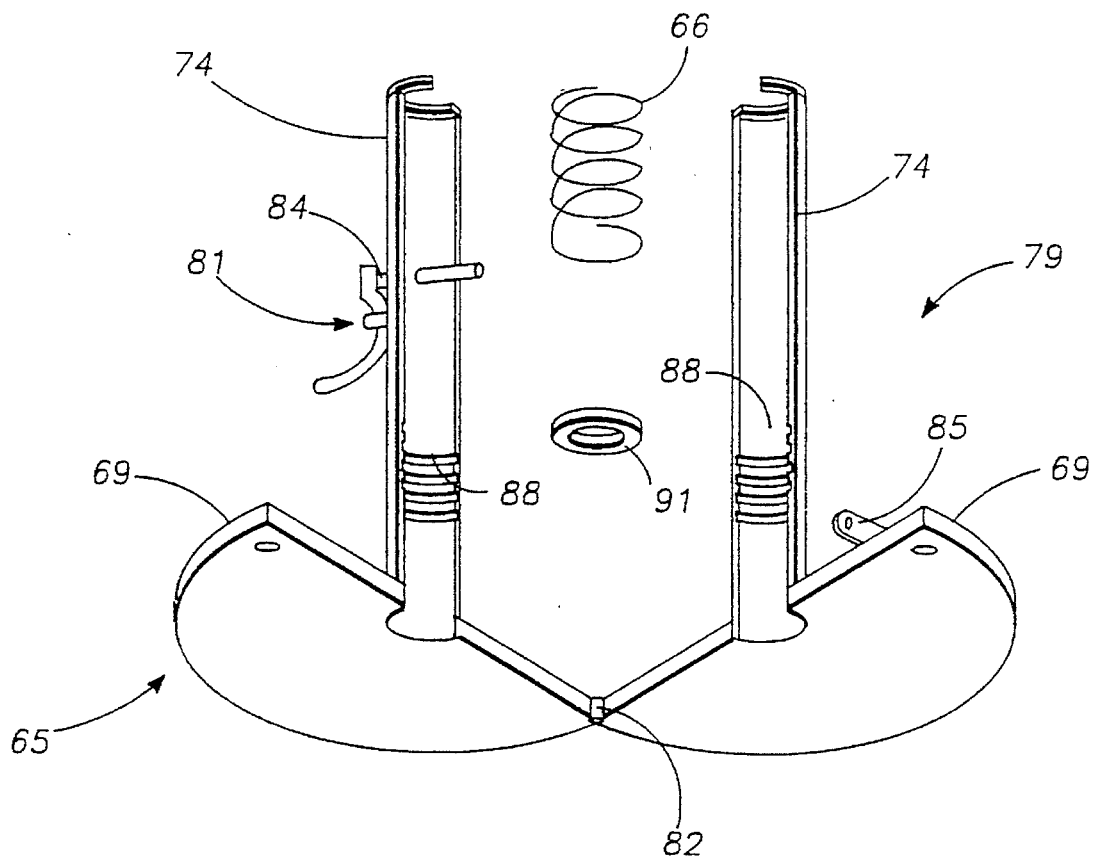
FIG. 11 shows an embodiment of a split housing for a trocar applicator.

Housing 65 comprises a lower pad 69 and a vertical frame 71 mounted on pad 69. Pad 69 is a disc-like plate having an orifice 72 through which trocar 47 can extend during insertion. The relatively large disc-like surface of pad 69 facilitates placement against patient 27 without entering the patient, and further orients trocar tube 47 for orthogonal penetration. Vertical frame 71 may comprise two (or more) vertically extending members 73 as shown, or comprise a enclosing column 74 as shown in FIG. 11, for example. Pad 69 is placed in contact with skin 42 at the insertion location. Preferably, one or more optional layers 76 may be provided on the skin contact surface of lower pad 69, such as a puncturable cover seal 77, and sterile pads 78, for example. The entire trocar tube 47 may be sealed within a sterile enclosing trocar applicator 63 which completely surrounds trocar tube 47 to maintain the sterility of pad 69, obdurator 64, trocar tube 47, and other elements prior to use.

Pad 69 and vertical frame 71 may be formed as an integral unit. FIG. 11 is an illustration of a trocar applicator 62 in which each of lower pad 69 and vertical enclosing column 74 are integral but comprise two separable sections 79, 81 adapted for easily attaching and removing trocar tube 47. A hinge 82 is provided so that the two halves of housing 65 can be easily opened to insert or remove trocar 47. A locking clip 85 is provided to secure the two haves of housing 65. Hinge 82 also facilitates adjustment of the trocar penetration depth as described below. Hinge 82 may be a separate conventional two part mechanical hinge or may be a structure formed into a molded plastic housing 65, such as a thinned wall region that facilitates bending.

In reference to FIGS. 6–10, spring 66 is provided for driving trocar-obdurator 63 through abdominal wall 24 and is mounted to, or retained within, vertical frame 71 of housing 65. Trigger 67 is for maintaining spring 66 in a deactivated or compressed condition when obdurator 64 is in its normally retracted position within applicator housing 65, and for activating or releasing spring 66 to drive trocar 47 into an exposed position capable of penetrating abdominal wall 24.

Trocar penetration limiting means is provided for limiting the distance trocar obdurator assembly 63 is driven (or penetrates) through abdominal wall 24, and may generally be located on vertical frame 71. Penetration limiting means permits safe insertion of trocar tube 47. Once trocar-obdurator assembly 63 has been driven into abdominal wall 24, additional penetration may be achieved if desired, by manually turning trocar-obdurator 63 while applying downward pressure. Exemplary detailed attributes of force means, trigger means, and penetration limiting means, are now described in the context of exemplary embodiments.

In a first embodiment of a trocar device 22, such as the embodiment illustrated in FIGS. 6–10, the force means comprises spring 66 mounted in the upper portion 83 of vertical frame 71, and trigger means comprising spring locking and releasing means for maintaining the spring in a compressed position and for releasing the spring upon a triggering command to drive the trocar tube downwardly through the skin and abdominal wall into abdominal cavity 28. In this embodiment, spring 66 is compressed and held in compressed condition by trocar tube 47. Pin 84 engages a receptacle 86 on the external surface of trocar tube 47 and is coupled to a pivoted lever 87. When pivoted lever 87 is pressed inward toward trocar tube 47, pin 84 is retracted from engaging receptacle 86, thereby releasing trocar tube 47 to move under the force of compressed spring 66.

While a compression-type spring 66 is shown, an extension-type spring with suitably altered attachment points may be used. Spring locking and releasing means may be other types of mechanical devices known in the art capable of holding spring 66 in a compressed condition and then releasing it.

Penetration distance limiting means 70 comprises internal threads 88 inside vertical frame 71 spaced apart from and below spring 66 which cooperates with elements of trocar assembly 63 including slip-ring 91 and flange 92, as described below. Threads 88 may be helical screw type threads or alternatively discontinuous annular grooves or rings. Threads 88 have a narrower separation between the two vertical support members 73 than the separation between the portions of vertical support members 73 between spring 66 and threads 88, so as to form a narrower neck or restriction 93 in frame 71. A relatively high friction surface may alternatively be used to lock slip-ring 91 into position within frame 71. The operation of coarse threads 88, annular rings or slots 90, or other high friction surface, are described in greater detail following a description of the trocar and obdurator elements.

FIG. 9 shows an exemplary structure of trocar and obdurator assembly 63 for use with trocar applicator 62. The illustrated trocar-obdurator assembly 63 is the same as that illustrated in FIGS. 6–7. Assembly 63 comprises a cylindrical trocar tube 47, trocar tube applicator engagement means for limiting the distance obdurator 64 is driven by spring 66 in applicator 62, obdurator 64, and obdurator locking means 94 for releasably locking the obdurator to the tube.

Cylindrical trocar tube 47 is an elongated hollow tube (cannula) having an inner surface 96 and an outer surface 97. As shown in FIG. 10, inner surface 96 has a locking channel 98 having a bend (approximately 90 degrees in this embodiment) which is adapted to removably engage a locking prong 94 on obdurator 64.

Trocar tube applicator engagement means, a flange 92, for limiting the distance obdurator 64 is driven by spring 66 through the abdominal wall 24 is attached to outer surface 97. Flange 92 is integral with the outer surface 97 of trocar tube 47 and extends a greater radial distance from the center of tube 47 than does the remainder of tube 47. Flange 92 may alternately extend around a partial or full circumference of tube 47, or comprise a single increase in diameter (e.g. a step) over a portion of tube 47, so that trocar tube 47 has a smaller diameter proximate obdurator 64 and a larger diameter distal to obdurator 64.

Flange 92 has a larger outer diameter than the inner diameter of slip-ring 91, so as to be unable to slide past slip-ring 91. In this way, the downward thrust of the trocar 47 can be adjustably controlled. Slip-ring 91 is adapted to adjustably engage the threads inside vertical frame 71 for adjusting the penetration distance of the trocar. Spiral-type mating threads provide means for adjusting the location of the slip-ring by rotating (screwing) the slip-ring relative to the mating threads in the vertical frame. The threads may have a fine or coarse pitch.

FIGS. 12–13 illustrate the manner in which slip-ring 91 acts as an adjustable stop for limiting the distance trocar 47 is driven by spring 66. The penetration distance is selected by locating the split-ring 91 within annular rings 90. Placing slip-ring 91 further away from pad 69 results in a shallow penetration depth, whereas placing slip-ring 91 closer to pad 69 results in a deeper penetration depth. The greater the initial distance between flange 92 and slip-ring 91, the farther trocar 47 can move before flange 92 engages slip-ring 91.

FIG. 12 illustrates the relatively shorter penetration distance of trocar/obdurator assembly 27 when slip-ring 91 is positioned near the top of vertical support 71. FIG. 13 illustrates the relatively greater penetration distance of trocar-obdurator assembly 63 when slip-ring 91 is positioned near the bottom of vertical support 71. FIGS. 12–13 show an embodiment wherein annular rings or slots 90 are provided rather than spiral screw-type coarse threads 88. In this embodiment, slip-ring 91 is fabricated in a thickness that permits mounting slip-ring 91 between neighboring annular rings or slots 90, thereby providing incremental distance adjustment.

Hinge 82 facilitates adjustment of penetration depth by allowing slip-ring 91 to be placed at the desired location within annular rings 90 of applicator 62, or within coarse threads 88 without requiring significant rotational adjustment, to set the penetration depth. The position is selected prior to activation of spring 66 so that obdurator 64 penetrates only to the desired depth.

Other means for compressing the spring and for maintaining the spring in a compressed condition without the necessity to insert the trocar-obdurator assembly 63 into the applicator and means for limiting the distance the trocar-obdurator 64 is driven by spring 66 may be provided. For example, in the embodiment illustrated in FIG. 14, differs in two ways from the embodiment illustrated in FIGS. 6–10.

In the embodiment illustrated in FIG. 14, a separate spring control means is provided for compressing the spring and for maintaining the spring in a compressed condition without the necessity to insert the trocar-obdurator assembly 63 into the applicator. Spring 66 is compressed and held in compressed condition by a retaining disk 95. Pin 84 engages a notch 100 on the external surface of retaining disk 95 and is coupled to a pivoted lever 87. When pivoted lever 87 is pressed inward toward the applicator housing, pin 84 is retracted from the notch 100. When a trocar tube 47 is inserted into the applicator, spring 66 extends to press disk 95 into contact with the upper end of the trocar tube, thereby moving trocar tube 47 under the force of spring 66. This structure permits the spring to be compressed prior to insertion of the trocar-obdurator assembly.

The embodiment in FIG. 14 also has an annular half-ring 101 formed integral to each vertical support member 73 at a fixed position. Half-rings 101 are employed, rather than a single continuous ring so that the two halves of the applicator housing can be opened at hinge 82, facilitating placement of the trocar prior to insertion and subsequent removal of the applicator from the inserted trocar. In this embodiment, trocar tube 47 has an enlarged flange 102 as illustrated in FIG. 12, which engages fixed half-rings 101 to limit the penetration depth of the trocar-obdurator into the abdominal wall. In the embodiment illustrated in FIG. 12, flange 102 is formed integral with the outside wall of the trocar at a predetermined position from the obdurator tip. As shown in FIGS. 15–16, trocar tubes having the flange at different locations may be selected at the time of trocar insertion to provide the desired penetration. For example, different trocar tubes may be fabricated having flange 102 located in 5–10 mm increments. Alternatively, another embodiment, such as that shown in FIG. 17 has a separate non-integral annular flange 102 having internal spiral threads (not shown) which mate to spiral threads 103 on the outside surface of trocar tube 47. The penetration distance is set by rotating flange 102 on the mating spiral threads to position the flange at a suitable distance from the obdurator tip. The spiral threads on the exterior surface of the trocar tube should have a sufficiently fine pitch so that the threads do not overly restrict the smooth entry of the trocar tube into the abdominal wall.

Obdurator 64 has a generally cylindrical shape to conform to the internal surface of trocar tube 47 .through which a portion of obdurator 64 extends. Obdurator has a sharp tip 105 capable of piercing abdominal wall 24. Sharp tip 105 extends past the front end 104 of tube 47 so that when applicator 62 drives trocar/obdurator assembly 63 forward, sharp tip 105 penetrates abdominal wall 24 first, A relative rapid driving force is required for proper penetration of obdurator 64 into abdominal wall 24. Slow penetration may undesirably compress the abdominal region rather than puncture it. The obdurator has a shape and size that permits it to be removed from the trocar tube after penetration of the abdominal wall by passing it back through the tube without removal the tube from the abdomen.

Obdurator locking means such as locking prong 94 is provided for removably locking obdurator 64 into position in tube 47. Prong 94 engages locking channel 98 on the inside surface of cylindrical tube 47. A handle 104 is provided for removing obdurator 64 from inside tube 47 after penetration. The handle should have a surface to facilitate grasping and hand turning and extend from the end of the trocar tube when inserted. The handle may be inserted after applicator 43 has been removed from the trocar-obdurator assembly. Handle 107 may be formed integral with obdurator 64 or be a detachable element which engages a slot within obdurator 64 permitting rotation of prong 94 out of channel 98 so that obdurator 64 may be lifted out of the interior of trocar tube 47.

Figure 18:
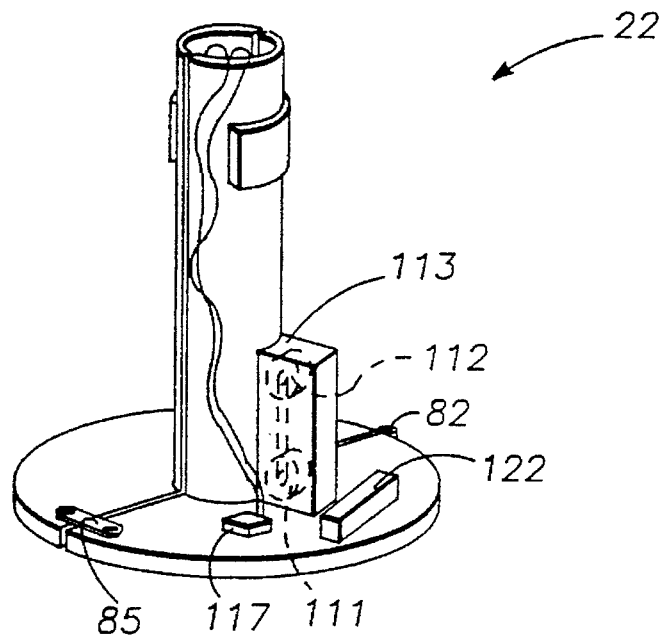
FIG. 18 shows an alternative embodiment of a trocar device having an electric motor to drive the trocar.

FIG. 18 illustrates the structure of a more sophisticated embodiment of trocar apparatus 22. In this embodiment force means comprises an electric motor 111 coupled to a traction wheel 112 for applying a tractional force to drive trocar/obdurator assembly 63 into and through abdominal wall 24. Traction wheel 112 may be a cylindrical wheel with a relatively high friction surface or may have gear teeth 113 on its circumferential surface 114. Trocar tube 47 has cooperating structure to engage wheel 112 including gear teeth 113 such as a toothed linear track 116.

In this embodiment, first electrical switch 117 is provided for triggering motor 111 to begin driving trocar-obdurator assembly 63. Second electric switch 118 is provided for limiting the penetration depth of the driven trocar 63. A single switch may be used for starting ad stopping driving of the obdurator; however, switches 117 and 118 are preferably different switches connected in electrical series so that both switches must be on for power to be delivered to motor 111. The provision of second switch 118 allows the penetration depth to be set before starting to drive the obdurator so that the obdurator is automatically stopped at the desired penetration depth, thereby eliminating risk the obdurator will be driven too deeply by a manually controlled stop switch. Second switch 118 may be a small switch, e.g. a microswitch, adjustably mounted on applicator 62.

A switch button engagement structure, such as a raised strip 119 on the external surface of trocar tube 47 slidably engages a switch button 121 on switch 118 to maintain switch 118 in an on condition. When switch button 121 travels far enough to move past the raised strip, button 121 disengages raised strip 119, and switch 118 is turned off. The location of raised strip 119 or alternatively of switch button 121 to adjust the penetration depth of the trocar assembly 63. Electric motor 111 is initially turned on to drive trocar 47 when switch 117 is turned on. However, when trocar 63 moves a distance sufficient to disengage raised strip 119 from switch button 121, first switch 118 turns off and disconnects power from motor 111. Removing power by turning switch 118 off, also stops or limits the movement of trocar and obdurator assembly 63. Motor 111 is preferably powered by battery 122, although other power sources consistent with the operating room environment and the patients safety may be used.

Figure 19:
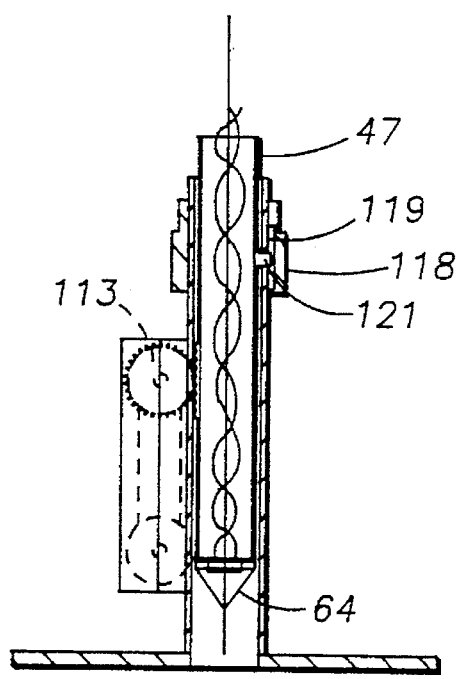
FIG. 19 shows a partial sectional view of the embodiment in FIG. 18.

FIG. 19 shows a more sophisticated trocar distance limiting means comprising a sonic transceiver or transducer 126 for transmitting sonic waves 127 into abdominal wall 24 and for receiving reflection signals 128 of the transmitted waves 127. Separate transmitter and receiver devices for the sonic waves may alternatively be used. One or more piezoelectric transducers may be used for transmitting and/or detecting the sonic waves, or other devices known in the art may be used.

Figure 20:
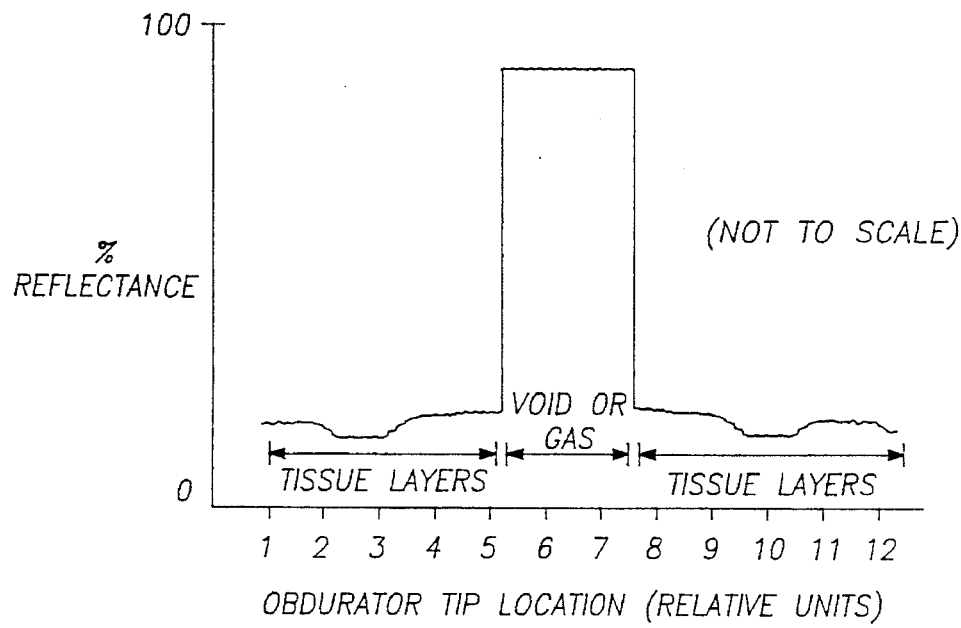
FIG. 20 is a graph, somewhat schematic, showing the change in expected sonic wave reflectance at a tissue-cavity boundary.

A sonic wave frequency (or frequencies) may be selected from a broad range frequencies to detect the boundary between the abdominal wall tissues and a void (or gas filled) body cavity region. The boundary is detected by sensing a sharp change in the sonic wave reflectance characteristics as illustrated in FIG. 20. The broad frequency range is suitable because of the great mismatch in acoustic impedance between a void (or gas filled) region, and a region of tissue (which has a relatively high water content). For example, sonic waves having acoustic frequencies between about 2 megahertz and about 12 megahertz may be used. These are the same frequencies commonly used in clinical acoustic imaging of the body. Somewhat higher or lower frequencies may also provide adequate boundary detection.

Sonic transceiver 126 may be removably located within obdurator 64 itself, such as within recess 129 at one end of obdurator 64, or the sonic waves may be directed through obdurator 64 by a more remote sonic transceiver. It is important however, that the reflected waves, or processed versions thereof, indicate the location of obdurator tip 105 so that motion can be arrested before the obdurator tip pierces too deeply into abdominal cavity 28.

Figure 21:
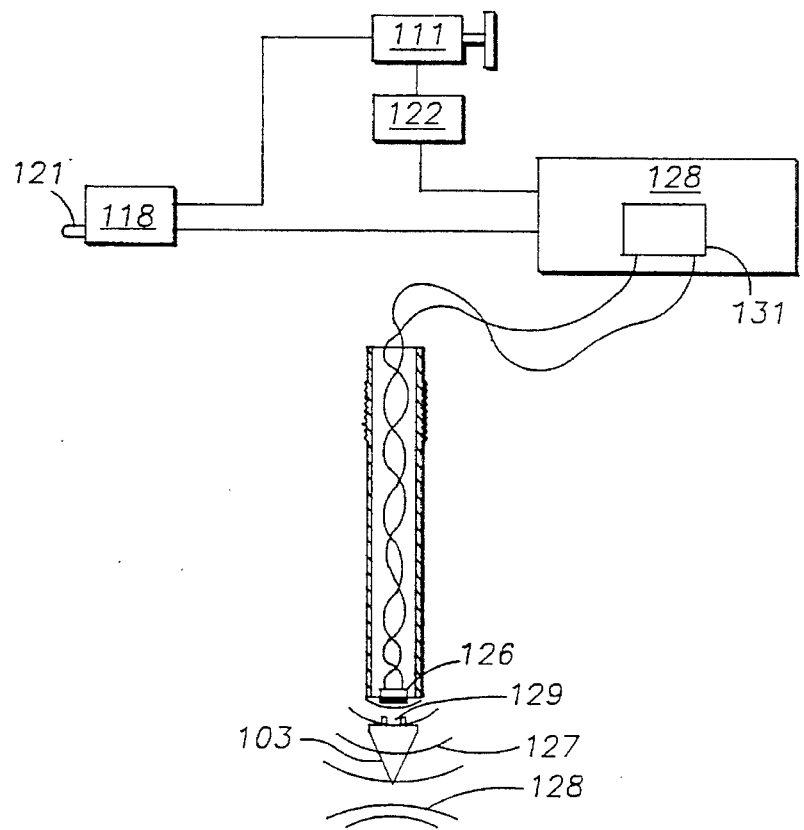
FIG. 21 shows an embodiment of a trocar obdurator assembly having a sonic transceiver to detect penetration of the abdominal cavity.

Signal analysis means for analyzing the reflection signals 128 and for determining when obdurator 64 traverses abdominal wall 24 and penetrates abdominal cavity 28 are also provided as illustrated in FIG. 21. Signal analysis means may comprise a simple electrical circuit 131, such as those that detect a threshold crossing, or that detect a signal phase change related to the transition, for example, or may comprise more sophisticated processing such as circuits incorporating a microprocessor with appropriate software or firmware algorithms.

Switch 117 for turning motor 111 off is interfaced to signal analysis means 131 and is responsive to signals from signal analysis means 131 to turn off motor 111 when obturator 64 has penetrated abdominal cavity 28. For example, when the signal analysis means 131 determines that the boundary between tissue and the void cavity has been reached, it cuts power to the trocar motor to stop penetration. In this way, the risk of obdurator tip 105 piercing any internal organs is diminished. Motor 111, switch 118, switch 117, signal analysis means 131, and any required power supplies are interfaced as is known in the art. A single integrated battery powered unit having the transducer and signal analysis means on board the trocar is preferred; however, if desired separate components, including the signal analysis means 131, may be provided remote from trocar applicator 62.

The trocar system 21 including rack 23 and trocar device 22 operates and is used as follows. Patient 27 is placed on supporting platform 48 prior to the surgical procedure. Cross beams 31 are adjustably positioned to span the external abdominal region 44 yet provide access to the trocar insertion site(s), and lowered by vertical supports 32 so that tape surface 41 applied to skin 42 is adhered to attaching arm 37. Cross beams 31 are then raised to separate abdominal wall 24 from abdominal viscera 26 and open a void space in the abdominal cavity 28. If desired, after making the appropriate incision, L-shaped rods 50 attached to cross beams 31 may optionally be used to aid in lifting and/or maintaining the separation. The patient is now ready for insertion of a trocar 22.

The approximate tissue depth 132 between the exterior abdominal skin 42 and the inner surface of the parietal peritoneum 43, is determined. The tissue depth 132 may be determined based on external physical characteristics of patient 27, or determined using other conventional techniques, such as ultra-sound measurements, for example.

Trocar device 22 (which is maintained in a sterile condition) is prepared by setting slip-ring 91 at the appropriate location within coarse threads 88 to set the penetration depth to allow the trocar to extend beyond the tissue depth 132. Trocar device 22 is then placed over the insertion site and held in place while trigger 67 is released causing spring 66 to drive trocar obdurator 64 into abdominal cavity 28. Obdurator 63 is then removed from within trocar tube 47. Applicator 62 is then removed from around trocar tube 47 by opening the clam-shell type housing 65 along hinge 82. Trocar mounting arm 51 is used for mounting trocar 47 to cross-beam 31 to maintain trocar tube 47 in a stable upright position. A surgical instrument may then be inserted and later removed through trocar tube 47.

In the embodiments having electric motor 111 rather than spring 66 to drive trocar-obdurator assembly 63, the operation is substantially the same except that the force means is triggered to drive the trocar-obdurator assembly into the abdomen by supplying electrical power to the motor and the penetration depth is limited by disconnect power form the motor.

In the embodiment having a sonic transceiver, the operation is substantially the same except that switch 117 for turning motor 111 off is responsive to signals from signal analysis means 131 and turns off motor 111 when the received reflection signals indicate that obdurator 64 has penetrated abdominal cavity 28.

It is evident from the above description, that a convenient low cost trocar system and method for using is provided which allows the user to safely raise the abdominal wall away from the viscera and to insert a trocar into the abdominal cavity of a patient.

The trocar surgical rack system advantageously provides for safe insertion of gas valve free trocars without insufflation of the abdominal cavity, and may also be used during insertion of conventional gas-valve type trocars. The rack system also advantageously holds an inserted trocar device upright after insertion, even with a surgical instrument in place, preventing the undesirable leaning that is often associated with conventional trocars. The number of trocars which may be used simultaneously is also increased, because the rack holds them stably in position and they do not require significant attention from surgical staff during the surgical procedure.

The trocar device according to the present invention advantageously provides a trocar that has an adjustable penetration depth for safety. The trocar device is also gas valve free so that the cost of each trocar is significantly reduced compared to gas-valve type trocars. Valve-free design also increases compatibility with a potentially larger set of surgical instruments since such instruments need not be compatible with a trocar valve. The low cost also permits disposal of each trocar after a single use when desired.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims and their equivalents.

All publications and patent applications cited in this specification are herein incorporated by reference as if each individual publication or patent application were specifically and individually indicated to be incorporated by reference.

What is claimed is:

1. A trocar applicator for applying a trocar to pierce an abdominal wall, said applicator comprising:

a housing comprising:

a lower pad having a orifice through which said trocar can extend; and a vertical frame mounted on said pad;

force means for driving said trocar through said abdominal wall, said force means mounted to said frame distal from said pad;

means for maintaining said force means in a deactivated position and for activating said force means to drive said trocar; and at a position intermediate between said pad and said force means attached to said vertical frame, trocar limiting means for limiting the distance said trocar is driven through said abdominal wall.

2. The trocar applicator as in claim 1, wherein said force means comprises a spring mounted in the upper portion of said vertical frame distal from said lower pad; and wherein said means for maintaining said force means is a trigger means for maintaining said force means in a deactivated position and for activating said force means to drive said trocar;

said trigger means comprising spring locking and releasing means for maintaining said spring in a compressed position and releasing said spring to drive said trocar downwardly; and wherein said trocar distance limiting means comprises an inwardly extending protrusion.

3. A trocar device for inserting a trocar through the abdominal wall and into the abdominal cavity of a patient, said trocar device comprising:

a trocar assembly comprising:

a cylindrical trocar tube;

trocar stopping means comprising an outwardly extending protuberance;

an obdurator extending through said cylindrical tube and having a sharp end extending past one of said ends of said cylindrical tube; and means for locking said obdurator into position within said tube; and an applicator device comprising:

a lower pad having a orifice through which said trocar can extend;

a vertical frame mounted on said pad;

force means for driving said trocar through said abdominal wall;

trigger means for maintaining said force means in a deactivated position and for activating said force means to drive said trocar;

trocar limiting means for limiting the distance said trocar is driven through said abdominal wall;

said vertical frame including a region having coarse internal threads spaced apart from and below said force means, said region having a narrower separation than the separation between other portions of said frame between said force means and said threaded region; and wherein said trocar limiting means comprises:

a slip-ring having an internal diameter larger than said cylindrical tube and extending inwardly sufficient to engage said protuberance, said slip ring is adapted to adjustably engage said coarse internal threads inside said vertical frame for adjusting said penetration distance;

whereby said cylindrical trocar tube is prevented from penetrating once said protuberance abuts said slip-ring.

4. The apparatus of claim 3, wherein said force means comprises an electric motor coupled to a traction wheel adapted to apply a tractional force to drive said trocar into said abdominal wall;

said trigger means comprises an electric switch means for selectively applying electrical energy to said electric motor to drive said trocar; and said limiting means further comprises an electric switch means for turning off said electric motor when said protuberance engages said slip ring.

5. The apparatus of claim 3, wherein said force means comprises a spring, and wherein said trocar limiting means is located at a position intermediate between said pad and said spring attached to said vertical frame.

6. A trocar device for inserting a trocar through the abdominal wall and into the abdominal cavity of a patient, said trocar device comprising:

a trocar assembly comprising:

a cylindrical trocar tube;

an obdurator extending through said cylindrical tube and having a sharp end extending past one of said ends of said cylindrical tube;

means for locking said obdurator into position within said tube; and an applicator device comprising:

a lower pad having a orifice through which said trocar can extend;

force means comprising an electric motor coupled to a traction wheel adapted to apply a tractional force to drive said trocar into said abdominal wall;

a vertical frame mounted on said pad;

an electric switch means for selectively applying electrical energy to said electric motor to drive said trocar;

trocar limiting means for limiting the penetration of said trocar comprising:

sonic transceiver means for transmitting sonic waves from said obdurator and for receiving reflection signals of said transmitted waves;

signal analysis means for analyzing said reflection signals and for determining when said obdurator traverses said abdominal wall and penetrates said abdominal cavity; and means responsive to said signal analysis means for controlling said electric motor to stop driving said trocar when said abdominal wall has been penetrated a predetermined distance.

7. A trocar applicator for applying a trocar to pierce an abdominal wall, said applicator comprising:

a housing comprising:

a lower pad having a orifice through which said trocar can extend; and a vertical frame mounted on said pad;

force means for driving said trocar through said abdominal wall, said force means mounted in said frame distal from said pad;

means for maintaining said force means in a deactivated position and for activating said force means to drive said trocar; and at a position intermediate between said pad and said force means attached to said vertical frame, trocar limiting means for limiting the distance said trocar is driven through said abdominal wall;

wherein said lower pad comprises a plurality of pad section connected by a first hinge means; and said vertical frame comprise a plurality of separable vertical sections adapted to separate from and join with one another to open and close a space between said vertical sections for inserting and removing said trocar.

8. A trocar device for inserting a trocar through a body wall and into the body cavity of a patient, said trocar device comprising:

an applicator comprising:

a pad adapted for placement adjacent said body wall and having a orifice through which said trocar can extend;

a vertical frame mounted on said pad;

force means attached to said vertical frame for driving said trocar toward said pad and through said body wall;

trigger means for maintaining said force means in a deactivated position and for activating said force means to drive said trocar; and trocar penetration limiting means for limiting the distance said trocar is driven by said force means; and a trocar assembly comprising:

a cylindrical trocar tube having two ends;

trocar stopping means for cooperating with said trocar limiting means to limit the distance said trocar is driven by said force means;

an obdurator extending through the interior of said cylindrical tube and having a sharp end extending past one of said ends of said cylindrical tube; and means for locking said obdurator into a predetermined position within said tube;

whereby said cylindrical trocar tube is prevented from being driven further into said body wall once said trocar stopping means cooperatively engages said trocar penetration limiting means.

9. The device as in claim 8 wherein:

said vertical frame includes a region having coarse threads spaced apart from said force means, said region having a narrower separation than the separation between other portions of said frame between said force means and said threaded region;

said trocar stopping means further comprising a protuberance outwardly extending from said cylindrical trocar tube; and said trocar penetration limiting means comprising:

a slip-ring having an internal diameter larger than the external diameter of said cylindrical tube and extending inwardly a sufficient distance to engage said protuberance, said slip-ring being adapted to be fixedly and adjustably coupled to said coarse threads of said vertical frame;

whereby engagement of said protuberance on said trocar with said adjustably positioned slip-ring fixedly coupled with said coarse threads to said frame as said trocar is driven by said force means stops said trocar from being driven further and prevents penetration of said trocar into said body cavity beyond a predetermined depth.

10. The apparatus of claim 9, wherein said force means comprises a spring and wherein said trocar limiting means is located at a position intermediate between said pad and said spring attached to said vertical frame.

11. The apparatus of claim 8, wherein said force means comprises an electric motor coupled to a traction wheel adapted to apply a tractional force to drive said trocar into said body wall;

said trigger means comprises an electric switch means for selectively applying electrical energy to said electric motor to drive said trocar; and said trocar limiting means comprises an electric switch means for turning off said electric motor when said trocar has been driven a predetermined distance.

\* \* \* \* \*